United States Patent
Napolitano et al.

(10) Patent No.: US 9,826,736 B2
(45) Date of Patent: Nov. 28, 2017

(54) QUATERNARY AMMONIUM CAPRYLYL GLYCOL DISINFECTANT WIPES

(75) Inventors: Lisa A. Napolitano, River Edge, NJ (US); Phyllis Vitolo, Saddle Brook, NJ (US); Michael V. Monticello, Paramus, NJ (US); Travis Duong, Toms River, NJ (US); Roy Blank, Spring Valley, NY (US)

(73) Assignee: Professional Disposables International, Inc., Orangeburg, NY (US)

( * ) Notice: Subject to any disclaimer, the term of this patent is extended or adjusted under 35 U.S.C. 154(b) by 769 days.

(21) Appl. No.: 12/855,485

(22) Filed: Aug. 12, 2010

(65) Prior Publication Data

US 2012/0039974 A1    Feb. 16, 2012

(51) Int. Cl.
| | |
|---|---|
| A01N 33/12 | (2006.01) |
| C11D 17/04 | (2006.01) |
| C11D 1/835 | (2006.01) |
| C11D 3/20 | (2006.01) |
| C11D 1/62 | (2006.01) |
| C11D 1/72 | (2006.01) |

(52) U.S. Cl.
CPC .............. *A01N 33/12* (2013.01); *C11D 1/835* (2013.01); *C11D 3/2041* (2013.01); *C11D 3/2044* (2013.01); *C11D 3/2068* (2013.01); *C11D 17/049* (2013.01); *C11D 1/62* (2013.01); *C11D 1/72* (2013.01)

(58) Field of Classification Search
None
See application file for complete search history.

(56) References Cited

U.S. PATENT DOCUMENTS

| | | | |
|---|---|---|---|
| 4,341,527 A * | 7/1982 | Zander et al. | ........... 436/66 |
| 5,440,094 A | 8/1995 | Zapletal | |
| 5,444,094 A | 8/1995 | Malik et al. | |
| 5,785,179 A | 7/1998 | Buczwinski et al. | |
| 5,908,854 A * | 6/1999 | McCue et al. | ........... 514/358 |
| 5,964,351 A | 10/1999 | Zander | |
| 6,030,331 A | 2/2000 | Zander | |
| 6,080,706 A | 6/2000 | Blanvalet et al. | |
| 6,090,771 A | 7/2000 | Burt et al. | |
| 6,123,953 A | 9/2000 | Greff | |
| 6,158,614 A | 12/2000 | Haines et al. | |
| 6,269,969 B1 | 8/2001 | Huang et al. | |
| 6,269,970 B1 | 8/2001 | Huang et al. | |
| 6,270,754 B1 | 8/2001 | Zhou et al. | |
| 6,273,359 B1 | 8/2001 | Newman et al. | |
| 6,566,574 B1 | 5/2003 | Tadros et al. | |
| 6,784,145 B2 | 8/2004 | Delambre et al. | |
| 6,841,090 B1 | 1/2005 | Serego Allighieri et al. | |
| 6,844,308 B1 | 1/2005 | Dastbaz et al. | |
| 6,951,834 B2 | 10/2005 | Mitra et al. | |
| 7,384,646 B2 | 6/2008 | Kobayashi et al. | |
| 7,582,681 B2 | 9/2009 | Schmaus et al. | |
| 7,632,871 B2 | 12/2009 | Kobayashi et al. | |
| 2005/0106191 A1 | 5/2005 | Kobayashi et al. | |
| 2007/0037721 A1* | 2/2007 | Michels et al. | ........... 510/295 |
| 2008/0142023 A1* | 6/2008 | Schmid et al. | ........... 128/849 |
| 2009/0175806 A1 | 7/2009 | Modak et al. | |
| 2009/0192231 A1 | 7/2009 | Lemons | |
| 2010/0069861 A1 | 3/2010 | Yao et al. | |

OTHER PUBLICATIONS

Dupont™ Spunlace Filtration Media 2008 one page.*
Hyamine 3500 reference 200 one page.*
International Search Report & Written Opinion of the International Searching Authority; Application No. PCT/US2011/046207; dated Dec. 5, 2011; dated Dec. 16, 2011; 12 pages.

* cited by examiner

*Primary Examiner* — Robert A Wax
*Assistant Examiner* — Caralynne Helm
(74) *Attorney, Agent, or Firm* — Lewis Roca Rothgerber Christie LLP

(57) ABSTRACT

A disinfectant wipe and disinfectant composition which exhibits exceptional antimicrobial activities as a result of the synergistic combination of a quaternary ammonium salts and 1,2-alkandiol is provided. The wipe is pre-impregnated with a disinfectant composition which comprises a quaternary ammonium salt, a 1,2-alkanediol with 5-10 carbon atoms, a glycol ether, a surfactant, a pH regulating agent, and water, and optionally alcohol. A method of preparation and a process for disinfecting a surface with the wipe composition are also provided.

6 Claims, No Drawings

QUATERNARY AMMONIUM CAPRYLYL GLYCOL DISINFECTANT WIPES

FIELD OF THE INVENTION

The present invention relates to disinfecting wipe products and compositions. More specifically, the invention relates to antimicrobial compositions, wipes pre-impregnated with the antimicrobial composition, methods of preparation, and processes for disinfecting surfaces with the compositions.

BACKGROUND OF THE INVENTION

Quaternary ammonium salts are broad-spectrum antimicrobial and antibacterial compounds commonly used in hard surface disinfectant products. They are typically available in commercial cleaning formulations with at least one surfactant and at least one organic solvent.

A particularly rigorous application of hard surface cleaning compositions is the class of hospital disinfectant products. Such products must be registered with the United States Environmental Protection Administration. Registration with the EPA requires submission of data establishing the disinfecting efficacy of the product. For example, DIS/TSS-1 Jan. 22, 1982 specifies the Efficacy Data Requirements for Disinfectants for Use on Hard Surfaces for hospital or medical environment claims. Label claims for use of disinfectants in hospital or medical environments are acceptable only for those products that are effective for general or broad-spectrum disinfection, particularly *Staphylococcus aureus* and *Salmonella enterica*, and additionally against the nosocomial bacterial pathogen *Pseudomonas aeruginosa*. In general, the test requirements for hospital disinfectant label usage require meeting the standards of the AOAC Germicidal Spray Products Test (Method No. 961.02), e.g., sixty carriers must be tested against each of *Salmonella enterica* ATCC 10708, *Staphylococcus aureus* ATCC 6538, and *Pseudomonas aeruginosa* ATCC 15442. For a product to be labeled as a disinfectant, it must kill 59 out of each set of 60 carriers, to provide effectiveness at the 95% confidence level. If the product is in the form of a towelette, the product will need to be tested in accordance with the test procedure specified in the American Society for Testing and Materials (ASTM) International's Standard Practice for Evaluation of Pre-saturated or Impregnated Towelettes for Hard Surface Disinfection (E2362-09), or the EPA's Standard Operation Procedure for Disinfecting Towelette Test against *Staphylococcus aureus, Pseudomonas aeruginosa*, and *Salmonella enterica* (SOP # MB-09-04, Revised Feb. 26, 2010).

A supplemental standard is also established under DIS/TSS-6 for Efficacy Data Requirements for Supplemental Efficacy Claims specifically, for labeling a product with an efficacy claim with respect to *Mycobacterium tuberculosis*. Effectiveness against *Mycobacterium tuberculosis* is a highly important quality for products used in cleaning medical inhalation therapy and/or pulmonary diagnostic equipment. The test requirement for making a labeling claim of effectiveness against *M. tuberculosis* is substantiating data derived on 10 carriers by the AOAC Tuberculocidal Activity Method (II Confirmative In Vitro Test for Determining Tuberculocidal Activity) for each of two (2) samples representing two (2) different batches of a liquid product under test. If the product is in the form of a towelette, the product will need to be tested in accordance with the test procedure specified in the American Society for Testing and Materials (ASTM) International's Standard Practice for Evaluation of Pre-saturated or Impregnated Towelettes for Hard Surface Disinfection (E2362-09), or the EPA's Standard Operation Procedure for Disinfecting Towelette Test against *Mycobacterium bovis* (BCG) (SOP # MB-23-01, Revised Feb. 26, 2010). To make the label claim, the tested product must kill the test microorganism on all carriers, and no growth in any of the inoculated tubes of two additional media is permitted. If a product has not met this standard it may not be sold absent a label recommendation which clearly excludes the use of the product on inhalation therapy and/or pulmonary diagnostic equipment or a statement that the product has not been tested for such activity.

In addition to germicidal efficacy, hospital disinfectant products should have low toxicity, low odor, non-flammability, low skin irritation and no staining upon contact with a surface, leave a minimum of discernible residue, clean well, and be competitively priced.

U.S. Pat. No. 5,444,094 to Stepan Company discloses a tuberculocidal composition which comprises a quaternary ammonium salt, a glycol ether at a range of 8 w/w % to 80 w/w %, a strong alkali compound such as sodium metasilicate, and a chelating agent such as ethylenediaminetetraacetate (EDTA). While the composition is able to kill tuberculosis-causing bacteria, it requires a medium to high level of the glycol ether and a strong alkali compound to enhance the germicidal effect of the quaternary ammonium salt, and it has not been shown to have 100% efficacy in killing tuberculosis-causing bacteria.

Thus, there continues to be a need in the hospital disinfectant market for disinfectant quaternary ammonium salt products that are efficient at killing tuberculosis-causing bacteria and provide rapid disinfecting properties after its application to a surface.

SUMMARY OF THE INVENTION

It is an object of the invention to provide a disinfectant cleaning product which is particularly useful for cleaning and disinfecting hard surfaces.

It is a further object of the invention to provide a disinfecting product which may be registered with the EPA as a hospital disinfectant product.

It is a further object of the invention to provide a disinfecting product which may be registered with the EPA as a tuberculocide thereby having efficacy against *Mycobacterium tuberculosis*.

In one aspect, the present invention is directed to be an antimicrobial wipe for disinfection of hard surfaces which comprises:

(a) an absorbent nonwoven substrate; and
(b) a liquid composition comprising, on a weight basis of the composition:
  a quaternary ammonium salt at a range of about 0.01 w/w % to about 1.0 w/w %, preferably about 0.1 w/w % to about 0.7 w/w %, and more preferably about 0.2 w/w % to about 0.5 w/w %;
  a 1,2-alkanediol with 5 to 10 carbon atoms at a range of about 0.05 w/w % to about 6.0 w/w %, preferably about 0.2 w/w % to about 1.5 w/w %, and more preferably about 0.4 w/w % to about 0.6 w/w %;
  a glycol ether at a range of about 0.5 w/w % to about 7.5 w/w %, preferably about 2.5 w/w % to about 6.0 w/w %, and more preferably about 4.0 w/w % to about 5.0 w/w %;
  a surfactant at a range of about 0.01 w/w % to about 3.0 w/w %, preferably about 0.05 w/w % to about 0.5 w/w %, and more preferably about 0.1 w/w %; optionally, alcohol at a range of about 0 w/w % to 60% w/w %; and the balance being water The combination of a 1,2-alkanediol with a quaternary ammonium salt composition provided by the present invention provides a uniquely effective hard surface disinfectant. While 1,2-alkanediols have been used as an emollient or another element of cosmetic and pharmaceutical products, they have not been used in hard surface disinfectant products due to their weak antimicrobial activity. The inventors have found, surprisingly, that 1,2-alkanediol, especially 1,2-octanediol, even at low concentrations, creates a synergistic effect when combined with the quaternary ammonium salt which greatly broadens and intensifies the antimicrobial activities of the composition. The resulting composition has been shown to meet EPA standards for hospital hard surface disinfectant products, including efficacy against tuberculosis-causing bacteria.

The substrate is impregnated with the composition at a loading level in the range from 1.5 xow to about 10 xow, preferably from about 2.5 xow to about 7.5 xow, and more preferably from about 3 xow to about 6 xow.

A preferred quaternary ammonium salt of the present invention is a mixture n-alkyl ($C_{12}$-$C_{18}$) dimethyl benzyl ammonium chloride and n-alkyl ($C_{12}$-$C_{14}$) dimethyl ethylbenzyl ammonium chloride, about 1:1 ratio. A preferred 1,2-alkanediol is 1,2-octanediol. A preferred glycol ether is dipropylene glycol mono-n-butyl ether or dipropylene glycol mono-n-propyl ether. A preferred surfactant is polyethylene glycol p-(1,1,3,3-tetramethylbutyl)phenyl ether. Preferably, a pH regulating agent is incorporated in the composition so that the pH of the composition is in the range of about 5.0 to about 11.5, preferably about 8.5 to about 11.0, and more preferably about 9.5 to about 10.5. A preferred pH regulating agent is a mixture of sodium hydroxide at about 0.03 w/w % and sodium carbonate at about 0.08 w/w % of the composition.

In yet another aspect, the present invention is directed to methods of preparation of the wipes. The methods start with mixing the components of the aforementioned composition until a homogenous solution or suspension is formed, followed by loading the resulting liquid composition onto a nonwoven water-insoluble substrate. The methods may further include packaging the loaded wipes into individual or bulk containers.

In a further aspect, the present invention is directed to processes for disinfecting surfaces which comprise the step of applying the aforementioned wipes to hard surfaces and allowing the contact between the compositions and the surfaces for a minimum contact time. The processes may optionally comprise a step of scrubbing, rinsing, wiping the surfaces, and combinations thereof.

DETAILED DESCRIPTION OF THE INVENTION

The composition, a wipe, methods of preparation, and processes for disinfecting surfaces in accordance with the present invention will now be discussed in detail. It should be noted that the invention in its broader aspects is not limited to the specific details, representative compositions, methods, and processes, and illustrative examples described in connection with the preferred embodiments and preferred methods. Modifications and equivalents will be apparent to practitioners skilled in this art and are encompassed within the spirit and scope of the appended claims.

The Disinfectant Wipes or Towelettes:

Disinfectant wipes or towelettes generally improve the performance of liquid disinfectants by providing mechanical cleaning properties and additional soil removal to complement the liquid disinfectants. They also allow for a significant reduction in the level of non-volatile surfactants and other adjuvants needed to achieve desired disinfecting results. Among different wipes or towelettes, especially disposable absorbent nonwoven wipes, provide versatility and convenience to users of the products.

The disinfectant wipes in accordance with the present invention comprise an absorbent nonwoven water-insoluble substrate impregnated with a disinfecting composition. The wipe substrate may be a sheet, pad, or multi-layer sponge product, and may be meant for use by itself or may be associated with an applicator handle or holder.

The nonwoven water-insoluble substrate for wipes may be made from plant-grown materials, or may be manufactured from processed plant-grown materials, or may be synthetic manmade materials. The nonwoven substrate can be made from the material such as viscose, rayon, polyester, wood pulp, polypropylene, polyethylene, nylon, or cotton.

Regardless of the material utilized to form the substrate, the basis weight of the substrate for the wipes is from about 10 grams per square meter (gsm) to about 200 gsm, preferably from about 20 gsm to about 100 gsm. The higher basis weight range is preferred due to higher loading capacity and heavier duty abilities in a hospital setting.

The substrate for the wipes in accordance with the present invention is loaded with the disinfecting composition at the loading level from about 1.5 times the original weight of the wipe ("xow") to about 10 times the original weight of the wipe, preferably from about 2.5 xow to about 7.5 xow, and more preferably from about 3 xow to about 6 xow.

The wipes may come in a variety of shapes, including but not limited to, circular, oval, square, rectangular, or irregularly shaped.

Each individual wipe may be arranged in a folded configuration and stacked one on top of the other to provide a stack of wet wipes. The folded configurations are well known to those skilled in the art and include c-folded, z-folded, quarter-folded configurations and so forth. Alternatively, the wipes are configured as continuous wipes perforated in a stack or roll for dispensing. The wipes can consist of one or more layers including an optional scrub layer for maximum cleaning efficiency.

The Disinfecting Compositions:

The disinfecting compositions in accordance with the present invention used with the wipe substrate preferably comprise the following components: a quaternary ammonium salt, a 1,2-alkanediol, a glycol ether, a surfactant, water, and optionally, a pH regulating agent.

Quaternary ammonium salt is used as a disinfecting agent for the compositions due to its broad spectrum of antimicrobial properties. The term "antimicrobial" used herein and in the appended claims refers to antibacterial, antifungal, antiviral and/or antinematode.

It is believed that quaternary ammonium salts act by disrupting the cell membrane of organisms and bacteria and thus kill the organisms and bacteria. Suitable quaternary ammonium salts have the following general formula:

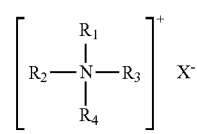

wherein $R_1$ and $R_2$ are straight or branched hydrocarbon chain having from one to seven carbon atoms; $R_3$ is a hydrocarbon chain having from eight to twenty carbon atoms, or a benzyl group; and $R_4$ is a hydrocarbon chain having from eight to twenty carbon atoms. The hydrocarbon chains of $R_3$ and $R_4$ can be branched or straight, and unsaturated or saturated.

Preferably, $R_1$ and $R_2$ are selected from the group consisting methyl, ethyl, propyl and mixtures thereof. More preferably, $R_1$ and $R_2$ are both methyl groups. Preferably, $R_3$ is a benzyl group, substituted or unsubstituted. More preferably, $R_3$ is an unsubstituted benzyl group. $R_4$ is a hydrocarbon chain preferably with ten to twenty carbon atoms, and more preferably, with twelve to eighteen carbon atoms.

The counterion X may be selected from, but not limited to, the group consisting of halogen, methylsulfate, cyclohexylsulphamate, saccharinate, carboxyl, and sulfonyl ions. Preferably, X is selected from the group consisting of chloride or bromide. More preferably, X is a chloride.

In preferred embodiments of the invention, the quaternary ammonium salt is alkyl dimethyl benzyl ammonium chloride (ADBAC), or alkyl dimethyl ethylbenzyl ammonium chloride (EBC), or a mixture thereof.

Other suitable quaternary ammonium compounds include dialkylmethyl amines quaternary salts (Dialkyl quats), and mixtures thereof, or mixtures with ADBAC or EBC quats. Other quaternary ammonium compounds such as are disclosed in U.S. Pat. No. 6,395,698, the disclosure of which is hereby incorporated by reference, may also be used.

In the most preferred embodiment, the quaternary ammonium compound is a mixture of n-alkyl ($C_{12}$-$C_{18}$) dimethyl benzyl ammonium chloride and n-alkyl ($C_{12}$-$C_{14}$) dimethyl ethylbenzyl ammonium chloride, where the n-alkyl ($C_{12}$-$C_{18}$) is composed with 60% $C_{14}$, 30% $C_{16}$, 5% $C_{12}$, and 5% $C_{18}$ and the n-alkyl ($C_{12}$-$C_{14}$) is composed with 68% $C_{12}$ and 32% $C_{14}$, which is available from Stephan Company under the trade name BTC 2125®M.

The quaternary ammonium salt in accordance with the invention can be present in an amount of about 0.01 w/w % to about 1.0 w/w %, preferably about 0.1 w/w % to about 0.7 w/w %, and more preferably about 0.2 w/w % to about 0.5 w/w %.

A 1,2-alkanediol is combined with the quaternary ammonium salt composition. Suitable 1,2-alkanediols are those with 5 to 10 carbon atoms, which include 1,2-pentandiol, 1,2-hexanediol, 1,2-heptanediol, 1,2-octanediol, 1,2-nonanediol, and 1,2-decanediol. Preferably, the 1,2-alkanediols are straight chain diols. The most preferred diol is 1,2-octanediol, also known as caprylyl glycol, which can be purchased from Jeen International Corporation under the product name JEECIDE CAP.

The 1,2-alkanediol in accordance with the invention can be present in an amount of a 1,2-alkanediol with 5 to 10 carbon atoms at a range of about 0.05 w/w % to about 6.0 w/w %, preferably about 0.2 w/w % to about 1.5 w/w %, and more preferably about 0.4 w/w % to about 0.6 w/w %.

As noted above, while 1,2-alkanediols have been used as an emollient or other element in cosmetic and pharmaceutical products, they have not been viewed as effective disinfectants and sanitizers due to their weak antimicrobial activity.

The inventors have found, surprisingly, that 1,2-alkanediol, especially 1,2-octanediol, creates a synergistic effect when combined with the quaternary ammonium salt which greatly broadens and intensifies the antimicrobial activities of the composition. The combination of the 1,2-alkanediol, such as 1,2-octanediol, and the quaternary ammonium salts in the disinfectant composition has been found to be significantly more effective than compositions which do not incorporate the 1,2-alkanediol. In particular, the combination of the 1,2-alkanediol and the quaternary ammonium salts in the disinfectant composition provides a significant antimicrobial effect against *Mycobacterium bovis* which is not obtained by compositions which lack the 1,2-alkanediol. The surprising effectiveness of the present invention makes it particularly useful in hospital hard surface applications, including particularly, applications where effectiveness against *Mycobacterium tuberculosis* is needed. As described in more detail below, it has been found that the wipes using the disinfectant composition were effective with a very short contact time, three minutes, and were able to completely disinfect test surfaces.

The synergistic combination of 1,2-alkanediol and the quaternary ammonium salt also allows for a significant reduction in the level of each ingredient needed to achieve excellent disinfecting results. In accordance with the present invention, the quaternary ammonium salt can be as low as 0.01 w/w % and the alkanediol can be as low as 0.05 w/w %. Since less residue is left behind after the disinfecting treatment, a surface treated with the composition can have excellent shine without rinsing or scrubbing.

Without wishing being bound by theory, we believe that 1,2-alkanediol, such as 1,2-octanediol, interacts with cell membranes due to its amphiphilic nature, and improves the ability of quaternary ammonium salts to attach and disrupt the cell membranes of organisms and bacteria and thus kill the organisms and bacteria.

Glycol ether is employed as a co-solvent of the composition. Suitable glycol ethers are those having excellent solvent properties, efficient at reducing surface tension of liquids, and reasonably soluble in water. Ideally, the glycol ethers are biodegradable.

In accordance with the present invention, all glycol ethers may be employed as solvents for the composition. The preferred glycol ether for the composition is selected from the group consisting of dipropylene glycol mono-n-propyl ether (DPnP) and dipropylene glycol mono-n-butyl ether (DPnB), which are commercially available from Dow Chemical Company under the trade name Dowanol DPnP and Dowanol DPnB, respectively. Other possible glycol ethers include diethylene glycol monobutyl ether, propylene glycol monomethyl ether, dipropylene glycol monomethyl ether, tripropylene glycol monomethyl ether, propylene glycol methyl ether acetate, dipropylene glycol methyl ether acetate, ethylene glycol monobutyl ether, diethylene glycol monobutyl ether, triethylene glycol monobutyl ether, diethylene glycol monoethyl ether, propylene glycol tertiary butyl ether, propylene glycol monobutyl ether, dipropylene glycol monobutyl ether, propylene glycol, and the like.

The glycol ether in accordance with the present invention may comprise from about 0.5 w/w % to about 7.5 w/w %, preferably about 2.5 w/w % to about 6.0 w/w %, and more preferably about 4.0 w/w % to about 5.0 w/w %.

Alcohol is optionally included as a co-solvent of the composition. The addition of alcohol is expected to further enhance the activity of the quaternary ammonium salt in the composition. The preferred alcohols are ethanol and isopropyl alcohol. Alcohols in accordance with the present invention may comprise from about 0.0 w/w % to about 60.0 w/w %, preferably about 5.0 w/w % to about 30.0 w/w %, and more preferably about 10.0 w/w % to about 20.0 w/w % of the composition.

To lower the interfacial tension between water and the glycol ether and to disperse the ingredients homogenously in the solution, an effective amount of a surfactant is added to the composition. It is preferred to select a low sodium, non-foaming or low foaming surfactant. It is also preferred to select a biodegradable surfactant.

The term "an effective amount" used herein and in the appended claims refers to a minimum amount of an ingredient which is sufficient to allow the ingredient to perform its desired function.

The surfactant for the present invention may be nonionic, anionic, cationic, zwitterionic and amphoteric. Preferably the surfactant is nonionic. The nonionic surfactant can be selected from, but not limited to, the group consisting of cetyl alcohol, steraryl alcohol, cetostearyl alcohol, oleyl alcohol, octaethylene glycol monododecyl ether, pentaethylene glycol monododecyl ether, decyl glucoside, lauryl glucoside, polyoxyethylene glycol octylphenol ethers, glycerol alkyl esters, glyceryl laurate, cocamide MEA, cocamide DEA, dodecyl dimethylamine oxide, and polyethylene glycol alkylphenyl ether. In one preferred embodiment, nonionic surfactant is polyethylene glycol p-(1,1,3,3-tetramethylbutyl)-phenyl ether, which is available from Dow Chemical Company, under the trade name Triton X-100. Mixtures of these nonionic surfactants may also be used.

Typically, the total amount of surfactants in accordance with the present invention is in the range of about 0.01 w/w % to about 3.0 w/w %, preferably about 0.05 w/w % to about 0.5 w/w %, and more preferably about 0.1 w/w %.

Testing has established that the synergistic antimicrobial activity of the combination of quaternary ammonium salts and 1,2-alkanediol intensifies with an increase in the pH of the composition. In contrast, the antimicrobial activity of quaternary ammonium salts alone does not improve with a pH variation. Without wishing being bound by theory, it is believed that 1,2-alkanediol is activated at a higher pH, which in turn activates the synergistic complex of quaternary ammonium salts and 1,2-alkanediol, and thus allows the quaternary ammonium salts, even at a low concentration, to act more quickly and effectively by attaching to and breaking down an outer cell membrane of the selected microorganisms.

Suitable pH regulating agents include, but not limited to, sodium hydroxide, potassium hydroxide, sodium carbonate, potassium carbonate, sodium metasilicate, mono-, di- and tri-alkane amines, basic buffers, and mixtures thereof. The pH regulating agent may be present in an amount sufficient to bring the composition to a predetermined pH range. A preferred pH regulating agent is a mixture of sodium hydroxide at about 0.03 w/w % and sodium carbonate at about 0.08 w/w %.

In accordance with the present invention, the pH of the composition is at a range of about 5.0 to about 11.5, preferably about 8.5 to about 11.0, and more preferably about 9.5 to about 10.5.

Water is the remaining component and is used in an amount to make up the final 100% w/w of the composition. Distilled or purified water, free of minerals, ions, and ion exchange components is preferred to prevent denaturing of active ingredients, such as the quaternary ammonium salts. The proportion of water in accordance with the invention is in the range of about 50 w/w % to about 98 w/w % of the composition, and preferably, from about 75 w/w % to about 95 w/w %.

It is believed that the combination of the glycol ether and water forms a hydrophilic layer which promotes a uniform distribution of the quaternary ammonium salt on a surface. Upon evaporation of water, the surface is coated with a layer of complex containing the evenly distributed quaternary ammonium salt, a 1,2-alkanediol, glycol ether and nonionic surfactant which provides the possibility of sustained germicidal activity for the surface. Advantageously, when biodegradable glycol ethers and nonionic surfactants are used, no removal of the residues is required. As such, the compositions are cost effective and environmental friendly.

The composition may further comprise a fragrance to mask the peculiar odor of 1,2-alkanediol. As used herein and in the appended claims, the term "fragrance" is used in its ordinary sense to refer to and include any non-water soluble fragrant substance or mixture of substances including natural, artificial and synthetically produced odoriferous substances. Typically, a fragrance is a mixture of various organic compounds such as alcohols, aldehydes, ethers, and aromatic compounds. The fragrance may have a fresh fruit odor or other pleasing odor.

While the precise composition of the fragrance is of no particular importance to the disinfecting performance, the amount of the fragrance added must be water miscible. The fragrance in accordance with the present invention may be present in an amount of about 0.4 w/w % to about 0.9 w/w %.

Additionally ingredients, which may be added to the compositions, further include an anti-forming agent, an antioxidant, a preservative, a builder, a chelating agent, a dye, a brightener, and combinations thereof.

The Methods of Preparation:

The methods of preparation comprise the step of formulating the disinfecting composition, the step of loading the composition to the wipe substrate, and optionally the step of packaging the wipe composition.

The disinfecting composition is prepared by mixing all ingredients of the composition in a suitable vessel or container until a homogenous suspension or solution is formed. As known to practitioners skilled in this art, the method of mixing may include stirring or other agitating means. It may also include heating the mixture to facilitate the mixing.

In one embodiment, the methods of formulation comprise the steps of mixing a surfactant at a range of about 0.01 w/w % to about 3.0 w/w %, preferably about 0.05 w/w % to about 0.5 w/w %, and more preferably about 0.1 w/w % with water; then mixing a glycol ether at a range of about 0.5 w/w % to about 7.5 w/w %, preferably about 2.5 w/w % to about 6.0 w/w %, and more preferably about 4.0 w/w % to about 5.0 w/w % with the surfactant/water mixture; then mixing a 1,2-alkanediol with 5 to 10 carbon atoms at a range of about 0.05 w/w % to about 6.0 w/w %, preferably about 0.2 w/w % to about 1.5 w/w %, and more preferably about 0.4 w/w % to about 0.6 w/w % with the glycol ether/surfactant/water mixture; then mixing a quaternary ammonium salt at a range of about 0.01 w/w % to about 1.0 w/w %, preferably about 0.1 w/w % to about 0.7 w/w %, and more preferably about 0.2 w/w % to about 0.5 w/w % with the 1,2 alkanediol/glycol ether/surfactant/water mixture; and lastly, a pH regulating agent is incorporated so that the pH of the composition is adjusted to the range of about 5.0 to about 11.5, preferably about 8.5 to about 11.0, and more preferably about 9.5 to about 10.5.

In accordance with the preferred embodiment of the present invention, the quaternary ammonium salt used in the aforementioned methods is preferably about 0.66 w/w %, the 1,2-alkanediol is preferably at about 0.55 w/w %, the glycol ether is preferably about 4.5 w/w %, the surfactant is preferably about 0.1 w/w %, a preferred pH regulating agent is a mixture of sodium hydroxide at about 0.03 w/w % and sodium carbonate at about 0.08 w/w %.

In accordance with the present invention, a preferred quaternary ammonium salt of the present invention is a mixture n-alkyl ($C_{12}$-$C_{18}$) dimethyl benzyl ammonium chloride and n-alkyl ($C_{12}$-$C_{14}$) dimethyl ethylbenzyl ammonium chloride, about 1:1 ratio, a preferred 1,2-alkanediol is 1,2-octanediol, a preferred glycol ether is dipropylene glycol mono-n-butyl ether or dipropylene glycol mono-n-propyl ether, a preferred surfactant is polyethylene glycol p-(1,1,3,3-tetramethylbutyl)phenyl ether, and a preferred pH regulating agent is a mixture of sodium hydroxide and sodium carbonate.

While no particular order of mixing the ingredients is necessary or required for the composition, it is preferred to add a surfactant or co-solvent into water first to assist the dissolution of the other ingredients. While several ingredients may be added to water simultaneously or pre-mixed prior to adding to water, it is preferred that only one ingredient is added each time to water and mixed until a clear aqueous solution or homogeneous suspension is obtained.

The methods of formulation may also comprise the step of mixing an optional ingredient in the water, wherein the optional ingredient is selected from the group consisting of an anti-forming agent, an antioxidant, a preservative, a builder, a chelating agent, a dye, a brightener, and combinations thereof.

The pH regulating agent is preferably added last to adjust the composition to a predetermined pH. The pH adjusting agent may be selected from, but not limited to, the group consisting of sodium hydroxide, potassium hydroxide, sodium carbonate, potassium carbonate, sodium metasilicate, mono-, di- and tri-alkane amines, basic buffers, and mixtures thereof.

The resulting liquid from the formulating is then loaded on a nonwoven water-insoluble substrate. The substrate can be made from the materials including, but not limited to, viscose, rayon, polyester, wood pulp, polypropylene, polyethylene, nylon, and cotton or blends of said materials. The basis weight of the substrate for the wipes is from about 10 grams per square meter (gsm) to about 200 gsm, preferably from about 20 gsm to about 100 gsm.

The methods of loading include, but not limited to, spraying, dipping, impregnation, saturating, and brush coating of the disinfecting liquid onto the nonwoven substrate. The loading time and manner may vary with respect to each loading method, as long as the loading level is controlled in the range from about 1.5 xow to about 10 xow, preferably from about 2.5 xow to about 7.5 xow, and more preferably from about 3 xow to about 6 xow.

Optionally, the methods of preparation may further comprise a packaging step. In one embodiment, the pre-moistened wipes are packaged as a continuous strip of material which has perforations between each wipe and which may be arranged in a stack or wound into a roll for dispensing. In another embodiment, the pre-moistened wipes are folded into c-folded, z-folded, or quarter-folded configurations and the like, and then stacked in a tub format and placed in the interior of a container or dispenser. Preferably, the container or dispenser is a sealed container. The container is desirably airtight and/or with a resealable opening to prevent evaporation of any of the components of the disinfectant composition. More preferably, each wipe is individually wrapped a sealed foil envelope or a sealed plastic envelope. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haines, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein in their entirety by reference thereto for all purposes.

The Methods for Disinfecting a Surface:

The methods of disinfecting a surface in accordance with the present invention comprise the step of applying an effective amount of the above described composition onto the surface. In preferred embodiments, the composition is applied with a disposable wipe. However, other applicators may be used, including sponges and similar products, or liquid dispensing devices such as spray dispensing containers that spray the composition onto the surface.

The disposable wipe of the preferred embodiment is a non-woven fabric such as viscose, rayon, polyester, wood pulp, polypropylene, polyethylene, nylon, or cotton, or blends of said materials. The fabric may be made from plant-grown materials, or may be manufactured from processes plant-grown materials, or may be synthetic man-made materials.

The basis weight of the wipe is from about 10 grams per square meter (gsm) to about 200 gsm, preferably from about 20 gsm to about 100 gsm. For a light duty disinfecting job, the disinfecting process typically requires wiping the soiled area only and lower basis weight wipes are usually employed for the job. For heavy duty disinfecting job, however, the cleaning process may require scrubbing, wiping, and combinations thereof, and accordingly industrial wipes, those with higher basis weight and/or an additional scrub layer, are preferred.

Unused wipes should be resealed to prevent evaporation of any of the components of the disinfectant composition. Preferably, each wipe is provided in a sealed foil envelope or a sealed plastic envelope. However, other packaging may be used, such as a plastic box with a resealable opening.

The present invention may be used to disinfect surfaces such as what are typically found in residential homes, nursing homes, hospitals, and public institutions, e.g., counter top, table top, sinks, bath tubs, tiles, walls, floors, glass, plastic, household appliances, and the like by wiping a soiled or infected surface with a pre-saturated wipe product.

When the composition uses biodegradable surfactants and glycol ethers and a low level of quaternary ammonium salts, and alkanediols, no rinsing is required to form a shiny disinfected surface. Therefore, the processes for disinfecting a surface may further comprise the step of allowing water to evaporate to form a layer of dried components coated on the surface for providing sustained disinfecting efficacy. However, the processes may optionally comprise the step of wiping away the residues or rinsing the surface after a short contact time between the composition and the surface. The contact time may be as little as three minutes.

It should be noted the present invention is not limited to the above descriptions as a person of skill in the art knows that the microbiocidal activity of a disinfecting composition may be manipulated by altering the concentration of its components, temperature, and contact time with a surface.

Efficacy of the Invention

The disinfection properties of the composition herein may be measured by the tuberculocidal effects of the composition. The disinfecting properties of the composition herein were studied as described below. An example formulation in accordance with the present invention, and a control formulation without capyrlyl glycol, as shown in Table 1 below, were tested for their tuberculocidal effects.

TABLE 1

Example Formulation and Control Formulation

| Ingredient | Example Formulation w/w % | Control Formulation w/w % |
|---|---|---|
| BTC 2125 ® M | 0.66 | 1.06 |
| Caprylyl glycol | 0.55 | 0.0 |
| Dowanol DPnP | 4.50 | 4.50 |
| Triton X-100 | 0.10 | 0.10 |
| Fragrance | <0.90 | <0.90 |
| Sodium hydroxide | 0.03 | 0.03 |
| Sodium carbonate | 0.08 | 0.08 |
| Water | 93.18 | 93.73 |

The efficacy of the invention was tested based on the methodology of the AOAC Tuberculocidal Activity Method as modified by the (ASTM) International's Standard Practice for Evaluation of Pre-saturated or Impregnated Towelettes for Hard Surface Disinfection (E2362-09). The organism studied was Mycobacterium bovis-BCG, which was obtained from the Organon Teknika Corporation, Durham, N.C. The Mycobacterium bovis-BCG was inoculated into fresh Modified Proskauer-Beck Media (MPB) and subjected to aerobic incubation at 35-37° C. to form a mature culture. The mature culture was transferred onto sterile surfaces of glass carriers and allowed to dry. Each carrier contained approximately $1.70 \times 10^5$ CFU (colony forming units) of Mycobacterium bovis—BCG. A film of Mycobacterium bovis-BCG cells dried on the surfaces of glass carriers was wiped with a wipe impregnated with the above test composition. The area of the wipe was rotated between each slide so as to expose a maximum amount of the wipe surface during the wiping procedure. Each inoculated carrier was treated with the wipe by passing over the carrier surface back and forth twice for a total of four passes. The carriers were held for exposure times of 3 and 5 minutes, and the wiping procedure was performed at staggered intervals to allow for the prescribed exposure time. After exposure, the carriers were transferred to 40 mL of neutralizer and then transferred to vessels containing neutralizing 40 mL of MPBM broth. 2.0 mL aliquots of the neutralizer were transferred to individual vessels containing 20 mL of Middlebrook 7H9 (7H9) and 20 mL of Kirchner's Medium (KM). Appropriate culture purity, sterility, inoculated carrier viability, carrier population, and neutralization confirmation were performed. Each subculture tube was incubated for 90 days at 35-37° C. The number of tubes that show growth of BCG was recorded at 31 days, 60 days, and 90 days. Control samples were simultaneously run to confirm that culture purity, viability, soil sterility, media sterility, carrier sterility, neutralization confirmation, and carrier population controls were all acceptable. Control tests were composed of a viability control test and neutralization confirmation control test. The neutralization controls in the subcultures showed growth, eliminating bacteriostasis as a cause of lack of growth in the test.

The efficacy of the formulation was evaluated by counting the visible number of carriers showing growth of Mycobacterium bovis-BCG in primary subcultures (in MPB medium) and secondary subcultures (in 7H9 and KM media) following a three or five minutes exposure to the formulation at room temperature (23.5° C.) in the presence of a 5% fetal bovine serum organic soil load. Table 2 demonstrates the test results of wipes according to the present invention:

TABLE 2

Test Results of Example Formulation

| Exposure Time | Subculture Media | Volume Subcultured | Total No. Carriers/Tubes Tested | Number Positive 31 days | 60 days | 90 days |
|---|---|---|---|---|---|---|
| 3 minutes | MPB | NA | 10 | 0 | 0 | 0 |
| | 7H9 | 2.0 mL | 10 | 0 | 0 | 0 |
| | KM | 2.0 mL | 10 | 0 | 0 | 0 |
| 5 minutes | MPB | NA | 10 | 0 | 0 | 0 |
| | 7H9 | 2.0 mL | 10 | 0 | 0 | 0 |
| | KM | 2.0 mL | 10 | 0 | 0 | 0 |

As can be seen, the testing of the example formulation was highly successful, with no recovery of the Mycobacterium bovis-BCG in either the 3 or 5 minute exposure test slides thereby meeting the acceptance criteria as required by the EPA.

In contrast, the control formulation which omitted the 1,2-alkanediol ingredient had much lower efficacy test results, as seen in the below table:

TABLE 3

Test Results of Control Formulation

| Exposure Time | Subculture Media | Volume Subcultured | Total No. Carriers/Tubes Tested | Number Positive 31 days | 60 days | 90 days |
|---|---|---|---|---|---|---|
| 3 minutes | MPB | NA | 10 | 0 | 4 | 5 |
|  | 7H9 | 2.0 mL | 10 | 0 | 0 | 0 |
|  | KM | 2.0 mL | 10 | 0 | 0 | 0 |
| 5 minutes | MPB | NA | 10 | 1 | 4 | 5 |
|  | 7H9 | 2.0 mL | 10 | 1 | 1 | 1 |
|  | KM | 2.0 mL | 10 | 0 | 0 | 0 |

As can be seen, the control formulation did not have the same results as the example formulation, and failed both the 3 and 5 minute exposure tests. The EPA acceptance criteria was not met for this formulation.

The comparison of Tables 2 and 3 clearly indicates a synergistically intensified antimicrobial effect occurs between a 1,2-alkanediol, such as 1,2-octanediol, and quaternary ammonium salts in the disinfectant composition of the invention as compared to composition lacking a 1,2-alkanediol.

Additionally, Table 2 reveals that wipes and compositions in accordance with the present invention meet the rigorous requirements for labeling for tuberculocidal effect.

Antibacterial wipes and compositions according to the invention are useful in the cleaning and/or disinfecting of surfaces, especially hard surfaces. The antimicrobial activity includes effects in sanitizing, disinfecting, and/or virucidal reduction of microorganisms, such as, for example, bacteria, viruses, fungi, and the like.

The present invention has improved efficacy against both Gram positive bacteria such as *Staphylococcus aureus* and Gram negative bacteria such as *Salmonella enterica*, as well as *Pseudomonas aeruginosa*. In addition, the present invention has been shown to have efficacy against tuberculosis-causing bacteria and the compositions of the invention should be usable in hospital environments for cleaning medical equipment, including inhalation therapy and/or pulmonary diagnostic equipment. Antimicrobial efficacy can be tested in accordance with the AOAC Germicidal Spray Products Test (Method No. 961.02), modified in accordance with the test procedure specified in the American Society for Testing and Materials (ASTM) International's Standard Practice for Evaluation of Pre-saturated or Impregnated Towelettes for Hard Surface Disinfection (E2362-09), or the EPA's Standard Operation Procedure for Disinfecting Towelette Test against *Staphylococcus aureus, Pseudomonas aeruginosa*, and *Salmonella enterica* (SOP # MB-09-04, Revised Feb. 26, 2010). Tuberculocidal activity may be tested in accordance with the AOAC Tuberculocidal Activity Method (II Confirmative In Vitro Test for Determining Tuberculocidal Activity) as modified by the ASTM or EPA SOPs for towelettes.

While described in terms of the presently preferred embodiments, it is to be understood that the present disclosure is to be interpreted as by way of illustration, and not by way of limitation, and that various modifications and alterations apparent to one skilled in the art may be made without departing from the scope and spirit of the present invention.

What is claimed is:

1. A method of disinfecting a surface having *mycobacterium* thereon comprising:
    applying an effective amount of a disinfecting composition onto a hard surface, using an applicator containing the disinfecting composition, said disinfecting composition comprising:
    about 0.01 w/w % to about 1.0 w/w % of $C_{12}$-$C_{18}$ alkyl dimethyl benzyl ammonium chloride, $C_{12}$-$C_{14}$ alkyl dimethyl ethylbenzyl ammonium chloride, or mixtures thereof;
    about 0.05 w/w % to about 6.0 w/w % of a 1,2-alkanediol;
    about 0.5 w/w % to about 7.5 w/w % of dipropylene glycol mono-n-butyl ether, dipropylene glycol mono-n-propyl ether, or mixtures thereof;
    about 0.01 w/w % to about 3.0 w/w % of a nonionic surfactant;
    a pH regulating agent to make the pH of the composition between about 5.0 and about 11.5; and
    water;
    wherein said disinfecting composition disinfects the hard surface and kills the *mycobacterium* thereon, and
    said disinfecting composition meets the United States Environmental Protection Agency's DIS/TSS-6 Efficacy Data Requirements for Supplemental Efficacy claims with respect to *mycobacterium tuberculosis*.

2. The method of claim 1, wherein the applicator comprises a wipe.

3. The method of claim 2, wherein the surface comprises a hospital area or hospital equipment.

4. The method of claim 2, where the surface is exposed to the disinfecting composition for at least three minutes.

5. The method of disinfecting a surface of claim 1, said method being effective to kill *mycobacterium* on the hard surface within 5 minutes of wiping the hard surface with the applicator containing the disinfecting composition.

6. The method of disinfecting a surface of claim 1, said method being effective to kill *mycobacterium* on the hard surface within 3 minutes of wiping the hard surface with the applicator containing the disinfecting composition.

* * * * *